United States Patent [19]

Schmidt et al.

[11] Patent Number: 5,120,533
[45] Date of Patent: Jun. 9, 1992

[54] TREATMENT OF ULCERS OF THE GASTROINTESTINAL TRACT USING DIMETHYLPOLYSILOXANE

[75] Inventors: Alfred Schmidt, Hamburg; Hans-Jürgen Upmeyer, Norderstedt, both of Fed. Rep. of Germany

[73] Assignee: Steigerwald Arzneimittelwerk GmbH, Darmstadt, Fed. Rep. of Germany

[21] Appl. No.: 528,078

[22] Filed: May 24, 1990

[51] Int. Cl.⁵ ............... A61K 31/765; A61K 31/695; A61K 9/20

[52] U.S. Cl. ................... 424/78.08; 424/441; 424/724; 514/925; 514/926; 514/927

[58] Field of Search ............... 424/78, 724; 514/819–820, 925–927

[56] References Cited

U.S. PATENT DOCUMENTS

| | | | |
|---|---|---|---|
| 2,934,472 | 4/1960 | May | 424/724 |
| 2,951,011 | 8/1960 | Feinstone | 167/55 |
| 3,422,189 | 1/1969 | Rider | 424/724 |
| 3,624,209 | 11/1971 | Granatek et al. | 514/927 |
| 4,127,650 | 11/1978 | Buehler | 514/789 |
| 4,396,604 | 8/1983 | Mitra | 514/960 |

FOREIGN PATENT DOCUMENTS

| | | |
|---|---|---|
| M6885 | 4/1969 | France . |
| A1097955 | 1/1968 | United Kingdom . |
| A2033915 | 5/1980 | United Kingdom . |

OTHER PUBLICATIONS

Dictionnaire Vidal, 1986, O.V.P. (Paris, FR) Seite 1361, Siligaz siehe den ganzen Artikel.

Primary Examiner—Thurman K. Page
Assistant Examiner—E. J. Webman
Attorney, Agent, or Firm—Nikaido, Marmelstein, Murray & Oram

[57] ABSTRACT

Dimethylpolysiloxane is effective in the treatment of ulcers of the gastrointestinal tract.

3 Claims, No Drawings

TREATMENT OF ULCERS OF THE GASTROINTESTINAL TRACT USING DIMETHYLPOLYSILOXANE

DESCRIPTION

The invention is in the area of the drug treatment of ulcerous disorders of the gastrointestinal tract.

The defoaming effect of dimethylpolysiloxane is well investigated and is already used therapeutically as antiflatulent or in preparation for sonography.

It has been found, surprisingly, that dimethylpolysiloxane can be employed with a particularly advantageous effect for the treatment of ulcerous disorders of the gastrointestinal tract. The defoaming effect of dimethylpolysiloxane is correlated with the other physicochemical properties film-formation and adhesion to walls. It has emerged, surprisingly, that dimethylpolysiloxane can also be administered orally over extended periods without disadvantageous effects in order to form and maintain in the oesophagus and in the gastrointestinal tract of humans a protective layer which assists the healing process when disorders of the type described are present.

The agent according to the invention is particularly employed for the treatment of ulcerous disorders of the qastrointestinal tract, generally of disorders of the oesophagus, of the stomach and upper small intestine, such as oesophagitis, ulcers (gastric and duodenal).

It is used in the form of an orally administerable composition with a pharmaceutically acceptable diluent or carrier, e.g. in the form of chewable tablets.

The use according to the invention of dimethylpolysiloxane experiences an increase in its effectiveness when the agent is taken in conjunction with silica gel.

This results in the coating which is generated by the agent in the oesophagus and gastrointestinal tract having a gel-like structure. This layer comes very close to the physiological mucus (e.g. gastric mucus) which protects the mucous membranes of the oesophagus and gastrointestinal tract.

It is possible with the agent employed according to the invention specifically to coat the mucous membranes of oesophagus and gastrointestinal tract over a prolonged period by appropriate intake even for days, weeks or months, and thus protect them against the aggressive constituents of the gastrointestinal tract, such as hydrochloric acid and digestive enzymes. The protection brought about by the agent employed according to the invention effects, on the one hand, a reduction in the activity of tissue-damaging mechanisms and, on the other hand, a comparatively unimpaired regeneration of the walls associated with the cell regeneration and with the ulcer cleansing. The agent employed according to the invention additionally brings about an increase in the pH (buffering of raised acid values) in the stomach. The subjective feeling of the patient improves due to intake of the agent, the 'heartburn', of the frequently hyperacid patients disappears.

INVESTIGATIONS

The following were investigated as a function of the dose and time:

1. Distribution and film-formation of dimethylpolysiloxane in the stomach.
2. Distribution and film-formation of dimethylpolysiloxane in the duodenum.

8 healthy men aged 25 and 40 years were employed as volunteer subjects (Table 1). The study was carried out as a controlled, randomized phase I study in crossover design. For the crossover design, the 8 subjects were randomized and assigned to the two dosage forms. The investigations were carried out at an interval of 7 days.

Two dosages were used per subject in the crossover design:

Dosage 1: 80 mg of dimethylpolysiloxane: (2×40 mg dimethylpolysiloxane chewable tablets)
Dosage 2: 160 mg of dimethylpolysiloxane: (4×40 mg dimethylpolysiloxane chewable tablets)

The composition of the dimethylpolysiloxane chewable tablets is shown in Table 8.

No other drugs were allowed to be taken immediately before and during the study. Furthermore, smoking was not permitted on the day of the investigation.

CONTROL INVESTIGATIONS

A comprehensive history was taken at the initial investigation; in addition the basic physical and neurological investigations. Laboratory tests were also carried out.

The following gastroenterological progress investigations were carried out on all the subjects on both investigation days:

1. Gastroscopy with documentation of oesophagus, stomach and duodenum immediately before chewing the dimethylpolysiloxane tablets.
2. The same investigations, including the documentation, 30 minutes after taking the chewable tablets.
3. The same investigations, including the documentation, 2 hours after chewing the dimethylpolysiloxane chewable tablets.

The investigations were carried out twice for each subject, with each alternative dosage, at an interval of 7 days. At a second progress investigation, in addition the pH of the stomach contents was measured at each gastroscopy.

The subjects were not allowed to take any food or drink for at least 6 hours before each drug intake and gastroscopy.

To prepare for the endoscopy, each subject received 0.5 mg of atropine in 1 ml of NACL solution administered subcutaneously. The local anaesthetic given for the mouth and pharyngeal space was Wander Novescine 1% solution (oxybuprocaine-HCL).

The gastroscopic investigations were carried out with an Olympus type $P_{10}$ instrument. Documentation was effected by the visual findings and photography.

RESULTS

1. Change in the stomach pH

Table 2 summarizes the changes in pH based on the pH at the investigation immediately before medication and 2 hours after medication.

The dimethylpolysiloxane administration leads to a distinct increase in the pH, i.e. a distinct shift from strongly acid in the direction of the alkaline range, irrespective of the number of chewable tablets administered. Despite the small number of subjects, this difference is significant at the 5% level.

Subject 7 was removed from the calculation because he had a duodenal cap greatly deformed by scarring and, moreover, the pH was already near the alkaline range (pH 6.05 or 6.83).

2. Film formation

Table 3 summarizes the individual results in Tables 4 to 7. The aim of the study was to demonstrate that the dimethylpolysiloxane remained in the stomach or duodenum in the observed period of 2 hours after administration of chewable tablets. The results are unambiguous. Administration of only 2 tablets of dimethylpolysiloxane (80 mg) leads to a reaction in all the subjects. This is even more evident due to administration of 4 tablets of dimethylpolysiloxane (160 mg).

At 360 mg, a relatively large amount of milky secretion was evident as observation parameter on the gastric mucous membrane in 7 of 8 subjects.

The individual findings (and the summary findings) are set out in Tables 4 to 7.

Evaluation of the visual findings and of the photographic documentation allows the summary assessment to be made that dimethylpolysiloxane chewable tablets and dimethylpolysiloxane are able to form an adhesive film on the gastric mucous membrane and in the proximal part of the duodenum.

TABLE 1

Anamnestic data on the subjects in the dimethylpolysiloxane study

|  | Mean | SD | Min | Max | Median |
|---|---|---|---|---|---|
| Age | 32.15 | 4.51 | 25 | 40 | 31.5 years |
| Height | 179.75 | 7.31 | 170 | 191 | 181 cm |
| Weight | 78 | 7.68 | 63 | 90 | 77 kg |
| Systol. blood pressure | 116 | 9.99 | 101 | 130 | 114.5 mmHg |
| Diast. blood pressure | 78.62 | 8.44 | 62 | 90 | 81 mmHg |
| Pulse | 63.5 | 10.94 | 53 | 88 | 60.5/min |

TABLE 8

40 mg dimethylpolysiloxane chewable tablets

Composition per tablet:

| I. | (1) Dimethylpolysiloxane DAB9 | 40.000 mg |
|---|---|---|
|  | (2) Highly disperse silica DAB9 | 12.555 mg |
|  | (3) Peppermint oil DAB9 | 0.300 mg |
|  | Aniseed oil DAB9 | 0.033 mg |
|  | (4) Microcrystalline cellulose DAB9 | 200.000 mg |
| II. | (5) Mannitol DAB9 | 338.111 mg |
|  | (6) Saccharin sodium DAB9 | 0.667 mg |
|  | (7) Carboxymethylcellulose sodium DAB9 | 1.667 mg |
| III. | (9) Magnesium stearate DAB9 | 3.333 mg |
|  | (10) Maize starch DAB9 | 3.333 mg |

DAB9 is the abbreviation for Deutches Arznei Buc (German Pharmaceutical Handbook) 9th Edition.

TABLE 2

Change in the pH values in the stomach on medication with dimethylpolysiloxane

| | Sub;. No. | | | | | | | |
|---|---|---|---|---|---|---|---|---|
| | 1 | 2 | 3 | 4 | 5 | 6 | 7 | 8 |
| Before med. | 1.80 | 1.96 | 1.92 | 1.98 | 1.51 | 2.11 | 6.03 | 1.69 |
| 30 min after med. | 2.06 | — | — | — | — | — | — | — |
| 2 hours after med. | 2.15 | 2.04 | 4.48 | 7.49 | 3.84 | 2.32 | 6.83 | 2.67 |
| No. of Tab. | 2 | 4 | 4 | 2 | 2 | 2 | 4 | 2 |

A positive influence on the pH by the medication is confirmed by the sign test ($p < 0.05$, two-sided). However, no influence of the number of tablets on the increase in the pH can be established.

Subject 7 has a deformed duodenal cap due to scarring, without stenosis, was not included in h calculation because of the high pH values.

TABLE 3

Positive reaction on administration of dimethylpolysiloxane chewable tablets 2 dimethylpolysiloxane tablets
Subjects with

| positive reaction* | no reaction | n |
|---|---|---|
| 8 | 0 | 8 |

*The reaction was minimal milky secretion in 5 of 8 subjects 4 dimethylpolysiloxane tablets
Subjects with

| positive reaction** | no reaction | n |
|---|---|---|
| 8 | 0 | 8 |

**The reaction was minimal milky secretion in 1 of 8 subjects, otherwise always a relatively large amount of milky secretion

TABLE 4

Findings at the first investigation

| | Time* | No. of tabl. | Finding |
|---|---|---|---|
| Subject No. 1 | 1 | 4 | Signs of antral gastritis. Otherwise duodenum, stomach and oesophagus macroscopically normal. |
| Subject No. 1 | 2 | 4 | Gastric juice in the fundus; milky, cloudy and flocculent. |
| Subject No. 1 | 3 | 4 | Only minimal residues in the fundus. Otherwise empty as far as the deep duodenum. |
| Subject No. 2 | 1 | 2 | Signs of slight antral gastritis. Otherwise duodenum, stomach and oesophagus macroscopically normal. |
| Subject No. 2 | 2 | 2 | Gastric juice in the fundus; milky, cloudy and flocculent |
| Subject No. 2 | 3 | 2 | Still milky substance in the fundus. Duodenum and antrum empty. |
| Subject No. 3 | 1 | 2 | Small hiatus hernia with reflux of grade 0–1. Otherwise duodenum, stomach and oesophagus macroscopically normal. |
| Subject No. 3 | 2 | 2 | Gastric juice in the fundus; milky, cloudy and flocculent |
| Subject No. 3 | 3 | 2 | Minute residues of milky, flocculent deposits. Fundus with a film-like coating over large areas. Duodenum empty. |
| Subject No. 4 | 1 | 4 | Duodenum, stomach and oesophagus macroscopically normal. |
| Subject No. 4 | 2 | 4 | Gastric juice in the fundus; milky, cloudy and flocculent |
| Subject No. 4 | 3 | 4 | Slightly cloudy, milky gastric juice. Otherwise duodenum, stomach, oesophagus normal. |
| Subject No. 5 | 1 | 4 | Small hiatus hernia with reflux oesophagitis (grade 0–I). Otherwise duodenum, stomach and oesophagus macroscopically normal. |
| Subject No. 5 | 2 | 4 | Antrum with scabby-milky coating in the fundus. Very cloudy, milky fluid. |
| Subject No. 5 | 3 | 4 | Residues of milky flakes in the fundus. A few plaques in the antrum. Duodenum empty. |
| Subject No. 6 | 1 | 4 | Duodenum, stomach and oesophagus normal. |

TABLE 4-continued

| | Findings at the first investigation | | |
|---|---|---|---|
| | Time* | No. of tabl. | Finding |
| Subject No. 6 | 2 | 4 | A few whitish, milky spots in the antrum. Otherwise cloudy, milky coating in the fundus. |
| Subject No. 6 | 3 | 4 | Very cloudy, milky fluid deposited on the fundus. A few plaques in the antrum. Duodenum empty. |
| Subject No. 7 | 1 | 2 | Deformed duodenal cap due to scarring, without stenosis. Stomach and oesophagus normal. |
| Subject No. 7 | 2 | 2 | Low-viscosity, milky deposits in the fundus. Antrum, duodenum empty. |
| Subject No. 7 | 3 | 2 | Minimal spots of milky deposits in the stomach fundus. Otherwise duodenum and antrum empty. |
| Subject No. 8 | 1 | 2 | Duodenum, stomach and oesophagus normal. |
| Subject No. 8 | 2 | 2 | Low-viscosity but cloudy, milky secretion in the fundus, film-like coating. Antrum, duodenum empty. |
| Subject No. 8 | 3 | 2 | Low-viscosity milky secretion as film-like coating. Secretion cloudy. Antrum, duodenum empty. |

*Time 1 = immediately before medication
Time 2 = ½ hour after medication
Time 3 = 2 hours after medication

TABLE 5

| | Findings at the second investigation (after 7 days) | | |
|---|---|---|---|
| | Time* | No. of Tabl. | Finding |
| Subject No. 1 | 1 | 2 | Duodenum, stomach, oesophagus normal, distinct macroscopic improvement in antral gastritis. pH 1.80 |
| Subject No. 1 | 2 | 2 | Distinctly less milky secretion and film coating. Otherwise finding unchanged. pH 2.06 |
| Subject No. 1 | 3 | 2 | Minimal milky secretion in the fundus. Duodenum, stomach normal. pH 2.15 |
| Subject No. 2 | 1 | 4 | Continuing signs of slight antral gastritis. Otherwise duodenum, stomach and oesophagus normal. pH 1.96 |
| Subject No. 2 | 2 | 4 | Large amount of high-viscosity milky, secretion in the fundus. Otherwise antrum empty. |
| Subject No. 2 | 3 | 4 | Large amount of high-viscosity milky secretion in the fundus. Antrum, duodenum empty. pH 2.04 |
| Subject No. 3 | 1 | 4 | Small hiatus hernia with reflux of grade 0-1. Otherwise duodenum, stomach and oesophagus macroscopically normal. pH 1.92 |
| Subject No. 3 | 2 | 4 | Large amount of high-viscosity milky secretion in the antrum and fundus, duodenum empty. |
| Subject No. 3 | 3 | 4 | Large amount of residues of milky coating and secretion in the antrum and fundus. Duodenum empty. pH 4.48 |
| Subject No. 4 | 1 | 2 | Duodenum, stomach and oesophagus macroscopically normal. pH 1.98 |
| Subject No. 4 | 2 | 2 | Minimal milky secretion in the fundus. Duodenum, antrum empty. |
| Subject No. 4 | 3 | 2 | Only residues of cloudy, milky secretion in fundus. Duodenum and antrum otherwise empty. pH 7.49 |
| Subject No. 5 | 1 | 2 | Small hiatus hernia with reflux oesophagitis (grade 0-1). pH 1.51 |
| Subject No. 5 | 2 | 2 | Minimal milky secretion in the corpus and in the antrum. Duodenum empty. |
| Subject No. 5 | 3 | 2 | Little cloudy secretion in the fundus. Antrum, duodenum empty. pH 3.84 |
| Subject No. 6 | 1 | 2 | Duodenum, stomach and oesophagus normal. pH 2.11 |
| Subject No. 6 | 2 | 2 | Little milky, cloudy secretion in the fundus and corpus. |
| Subject No. 6 | 3 | 2 | Minimal secretion in the duodenum and in the stomach. pH 2.32 |
| Subject No. 7 | 1 | 4 | Deformed duodenal cap due to scarring, without stenosis. Stomach and oesophagus normal. pH 6.03 |
| Subject No. 7 | 2 | 4 | Little milky cloudy secretion in the fundus. Antrum duodenum empty. |
| Subject No. 7 | 3 | 4 | Minimal secretion in the fundus without the milky cloudiness. Duodenum, antrum empty. pH 6.83 |
| Subject No. 8 | 1 | 4 | Duodenum, stomach and oesophagus normal. pH 1.69 |
| Subject No. 8 | 2 | 4 | Minimal, milky secretion as film-like coating. Tablets unchewed in the corpus. Duodenum empty. |
| Subject No. 8 | 3 | 4 | Now large amount of cloudy, milky secretion as film-like coating in the fundus. Corpus, duodenum, antrum empty. pH 2.67 |

*Time 1 = immediately before medication
Time 2 = ½ hour after medication
Time 3 = 2 hours after medication

TABLE 6

Summary of the findings in the dimethylpolysiloxane study

| | No. of subj. | Frequency of occurrence | | | | |
|---|---|---|---|---|---|---|
| | | 2T | 4T | t2 | t3 | t 2 + 3 |
| Signs of antral gastritis | 2 | | | | | |

TABLE 6-continued

Summary of the findings in the dimethylpolysiloxane study

| | No. of subj. | Frequency of occurrence | | | | |
|---|---|---|---|---|---|---|
| | | 2T | 4T | t2 | t3 | t 2 + 3 |
| Antral gastritis macroscop. improved | 1 | | | | | |
| Duodenum and antrum empty | 6 | 6 | 4 | | 4 | 6 |
| Duodenum empty | 3 | | 3 | 1 | 2 | |
| Corpus empty | 1 | | 1 | | 1 | |
| Minimal/little milky secretion | 6 | 5 | 1 | 2 | 2 | 2 |
| Minimal/residues of spots of milky deposits | 4 | 2 | 2 | 1 | 3 | |
| A few plaques in the antrum | 2 | 0 | 2 | 0 | 2 | |
| Milky, cloudy, flocculent gastric juice | 4 | 2 | 2 | 2 | | 2 |
| Milky deposits | 5 | 3 | 2 | 2 | 1 | 2 |
| Large amount of high-viscosity milky secretion | 3 | 0 | 3 | 1 | 1 | 1 |
| Large amount of residues of milky coating and secretion | 1 | 0 | 1 | | 1 | |

Abbreviations:
No. of subj. = number of subjects;
T = tablets;
t = time

TABLE 7

Findings in the dimethylpolysiloxane study

| | Subj. No. | Date | No. of tabl. | Investigation time |
|---|---|---|---|---|
| Signs of antral gastritis | 1 | March 15 | | 1 |
| Antral gastritis macroscop. improved | 1 | 22.3. | | 1 |
| Signs of antral gastritis | 2 | March 15 | | 1 |
| | 2 | 22.3. | | 1 |
| Small hiatus hernia | 3 | March 15 | | 1 |
| | 3 | 22.3. | | 1 |
| | 5 | March 15 | | 1 |
| | 5 | 22.3. | | 1 |
| Deformed duodenal cap due to scarring, without stenosis. | 7 | March 15 | | 1 |
| | 7 | 22.3. | | 1 |
| Duodenum and antrum empty | 2 | March 15 | 2 | 3 |
| | 3 | March 15 | 2 | 3 |
| | 4 | 22.3. | 2 | 2 and 3 |
| | 5 | 22.3. | 2 | 2 and 3 |
| | 7 | March 15 | 2 | 2 and 3 |
| | 8 | March 15 | 2 | 2 and 3 |
| | 2 | 22.3 | 4 | 2 and 3 |
| | 4 | March 15 | 4 | 3 |
| | 7 | 22.3. | 4 | 2 and 3 |
| | 8 | 22.3. | 4 | 3 |
| Duodenum empty | 5 | March 15 | 4 | 3 |
| | 6 | March 15 | 4 | 3 |
| | 8 | 22.3. | 4 | 2 |
| Corpus empty | 8 | 22.3. | 4 | 3 |
| Minimal milky secretion (tablets unchewed in the corpus) | 8 | 22.3. | 4 | 2 |
| Minimal milky secretion in the fundus | 1 | 22.3. | 2 | 2 and 3 |
| | 4 | 22.3. | 2 | 2 and 3 |
| | 5 | 22.3. | 2 | 3 |
| | 6 | 22.3. | 2 | 2 |
| Minimal milky secretion in the corpus and antrum | 5 | 22.3. | 2 | 2 |
| | 6 | 22.3. | 2 | 2 |
| Fundus with minimal spots of milky deposits | 7 | March 15 | 2 | 3 |
| | 1 | March 15 | 4 | 3 |
| Little milky secretion in the fundus | 7 | 22.3. | 4 | 2 |
| Stomach with minimal spots of milky deposits | 7 | March 15 | 2 | 3 |
| Minimal secretion in the duodenum and antrum | 6 | 22.3. | 2 | 3 |
| Minimal secretion in the fundus without milky cloudiness | 7 | 22.3. | 4 | 3 |
| A few whitish spots in the antrum | 6 | March 15 | 4 | 2 |
| Minute residues of milky, flocculent deposits | 3 | March 15 | 2 | 3 |
| Residues of milky flakes in the fundus | 5 | March 15 | 4 | 3 |
| A few plaques in the antrum | 5 | March 15 | 4 | 3 |
| | 6 | March 15 | 4 | 3 |
| Milky, cloudy, flocculent gastric juice in the fundus | 2 | March 15 | 2 | 2 and 3 |
| | 3 | March 15 | 2 | 2 |
| | 1 | March 15 | 4 | 2 |
| | 4 | March 15 | 4 | 2 and 3 |
| Low-viscosity, milky deposits in the fundus | 7 | March 15 | 2 | 2 |
| | 8 | March 15 | 2 | 2 and 3 |
| Fundus with film-like coating over large area | 3 | March 15 | 2 | 3 |
| Antrum and fundus with scabby-milky coating | 5 | March 15 | 4 | 2 |
| Fundus with cloudy, milky coating | 6 | March 15 | 4 | 2 and 3 |
| Large amount of high-viscosity milky secretion in the fundus | 2 | 22.3. | 4 | 2 and 3 |
| | 3 | 22.3. | 4 | 2 |
| Large amount of high-viscosity milky secretion in the antrum | 3 | 22.3. | 4 | 2 |
| Large amount of cloudy, milky secretion as film-like coating in the fundus | 8 | 22.3. | 4 | 3 |
| Large amount of residues of milky coating and secretion in the fundus. | 3 | 22.3. | 4 | 3 |
| Large amount of residues of milky coating and secretion in the antrum | 3 | 22.3. | 4 | 3 |

Dimethylpolysiloxane is obtained by hydrolysis and polycondensation of dichlorodimethylsilane and chlorotrimethylsilane. The various types differ in the nominal viscosity which is expressed by the number with the substance name.

The degree of polymerization (n=20 to 400) is such that the kinematic viscosity ranges from 20 to 1,000 mm$^2 \cdot$s$^{-1}$ (20 to 1,000 cSt).

The structural formula of dimethylpolysiloxane is:

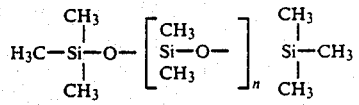

S 184 silicone antifoam agent from Wacker Chemie was used to prepare the chewable tablets in the tests described hereinbefore. Equivalent results are also achieved with dimethylpolysiloxane or silicone oils with a kinematic viscosity in the range from 100 to 10,000 mm$^2 \cdot$s$^{-1}$, in particular 300 to 3,000 mm$^2 \cdot$s$^{-1}$.

Aerosil 2000 was employed as highly dispersed silica.

We claim:

1. A method of treating a gastric or duodenal ulcer in a patient in need of such treatment, which comprises orally administering to the patient a composition consisting essentially of an ulcer-treating effective amount of dimethylpolysiloxane.

2. A method according to claim 1 wherein the dimethylpolysiloxane has a kinematic viscosity in the range of 100 to 10,000 mm$^2 \cdot$s$^{-1}$.

3. A method according to claim 1 wherein the composition contains silica gel.

* * * * *